United States Patent [19]
Egner

[11] Patent Number: 6,013,137
[45] Date of Patent: Jan. 11, 2000

[54] PROCESS AND DEVICE FOR TREATING SCREENINGS FROM THE MECHANICAL CLEANING STAGE OF A SEWAGE TREATMENT PLANT

[75] Inventor: Siegfried Egner, Adelsheim, Germany

[73] Assignee: Egner Umwelttechnologie GmbH, Adelsheim, Germany

[21] Appl. No.: 08/945,433

[22] PCT Filed: Apr. 11, 1996

[86] PCT No.: PCT/DE96/00640

§ 371 Date: Mar. 6, 1998

§ 102(e) Date: Mar. 6, 1998

[87] PCT Pub. No.: WO96/33134

PCT Pub. Date: Oct. 24, 1996

[30] Foreign Application Priority Data

Apr. 20, 1995 [DE] Germany ............................ 195 14 608
Apr. 20, 1995 [DE] Germany ....................... 295 06 702 U
Jul. 8, 1995 [DE] Germany ............................ 195 24 893

[51] Int. Cl.[7] ................................ B08B 7/04; A61L 2/00; A61L 2/12
[52] U.S. Cl. ................................ 134/1; 134/226; 134/30; 134/34; 134/37; 134/42; 422/21
[58] Field of Search .................................. 134/1, 26, 30, 134/37, 42, 34; 422/21

[56] References Cited

U.S. PATENT DOCUMENTS 3,523,076  8/1970  Goerz et al. .
3,670,891  6/1972  Allen .
4,565,669  1/1986  Collins et al. ............................ 422/78
4,631,133  12/1986  Axelrod ................................. 210/739
5,389,114  2/1995  Forder ...................................... 44/552

FOREIGN PATENT DOCUMENTS 2 326 030  12/1973  Germany .

OTHER PUBLICATIONS

Dictionary of Science and Technology, W & R Chambers, p. 757, 1974.

*Primary Examiner*—Randy Gulakowski
*Assistant Examiner*—Alexander Markoff
*Attorney, Agent, or Firm*—Darby & Darby

[57] ABSTRACT

A process and, respectively a device, for treating screenings from the mechanical cleaning stage of a sewage treatment plant is defined in that the screenings have electromagnetic waves in the frequency range between 1 GHz (gigahertz) and 1 THz (terahertz), so-called microwaves, applied to them for a predeterminable period.

3 Claims, 1 Drawing Sheet

PROCESS AND DEVICE FOR TREATING SCREENINGS FROM THE MECHANICAL CLEANING STAGE OF A SEWAGE TREATMENT PLANT

TECHNICAL FIELD

The present invention relates to a process and a device for treating screenings from the mechanical cleaning stage of a sewage treatment plant.

The screenings arising at the end of a mechanical cleaning stage of a sewage treatment plant are often infected with bacteria and viruses. These screenings therefore have to be disinfected, so that no risk to the environment, in particular to humans, occurs in the following treatment stages or in the case of landfill.

PRIOR ART

In order to disinfect screenings, it is known to use chemical agents, but this gives rise to the problem of how these agents can be mixed with the screenings without great outlay on apparatus. There are therefore always areas in which the chemical agents do not act on the screenings, and thus in these areas there is inadequate disinfection with the inherent hazard potential. However, admissible mixing may be achieved only with a great deal of outlay, which is generally not tolerable.

DESCRIPTION OF THE INVENTION

The present invention is based on the technical problem or, respectively, the task, proceeding from the cited prior art, of specifying an improved process and an improved device for treating screenings from the mechanical cleaning stage of a sewage treatment plant which, with an economically tolerable outlay on apparatus, ensures reliable disinfection as far as the killing of viruses and can be used commercially.

Accordingly, the method according to the invention is distinguished by the fact that, within the framework of a disinfection stage, the screenings have electromagnetic waves in the frequency range between 1 GHz (gigahertz) and 1 THz (terahertz), so-called microwaves, applied to them for a predeterminable period, during or after the treatment the screenings are subjected to an airstream, which results in convective drying of the screenings and the air is guided through in one pass or in a circulation, and the screenings are washed or pressed before the disinfection stage and are dried or compacted after the disinfection stage. In this case, the application takes place at the end of the cleaning stage, screenings themselves are disinfected and the water which is present at the start of the cleaning stage in the sludge/solid mixture is not simultaneously disinfected, since the "biology" present in this water is intended to be retained for the further sewage treatment process. The drawing process leads to a reduction in weight of the screenings that subsequently have to be transported further. Furthermore, the dry screenings lead to lower contamination of equipment coming into contact with the screenings following the drying.

Use is preferably made of microwaves which lie in the frequency range between 2.425 and 2.475 GHz (gigahertz), this range also commonly being used in a microwave cooker. During the disinfection operation, the screenings are heated by the action of the microwaves in a cavity formed by a housing, the microwaves being fed into the cavity resonator by a magnetron. As a result of dielectric losses in the screenings, energy is taken from the microwave field and the screenings are consequently heated, which results in the killing of viruses at sufficiently high temperatures.

A preferred design variant, which is used advantageously in particular with respect to a favorable energy balance, is distinguished by the fact that, in a heating-up phase, the screenings have a magnetic field with a high energy density applied to them and, in a heat-maintaining phase, have a magnetic field with a lower energy density applied to them.

The device according to the invention for treating screenings from the mechanical cleaning stage of a sewage treatment plant, having a screenings inlet area and a screenings outlet area, is distinguished by the fact that a device generating electromagnetic waves, a so-called microwave device, is provided, which generates electromagnetic waves in the frequency range from 1 GHz (gigahertz) to 1 THz (terahertz) and applies these to the screenings for a predeterminable period, and an air movement device is provided, which subjects the screening to an airstream during or after the treatment, a low-pressure fan preferably being used for the air movement device. As a result of the provision of an air movement device, a convective drying operation is set in motion, which results in accelerated drying of the screenings. This drying operation can be performed both in the reactor space in which the screenings are heated and in any post-heating space which may be present. A filter unit is preferably connected upstream or downstream of the air movement device, in order to prevent the formation of an unpleasant odor outside the plant. As a result of the fact that the treated screenings have a higher level of dryness, their raw weight decreases, which overall has a favorable effect on the subsequent compaction operation and the transport to the landfill or incineration plant.

An advantageous refinement of the device according to the invention is distinguished by the fact that in the area of the device for generating the microwave rays the device has thermal insulation. This is particularly advantageous with respect to the amounts of energy to be used for reliable disinfection.

Further embodiments and advantages of the invention emerge through the features further listed in the claims, as well as through the exemplary embodiments indicated below. The features of the claims can be combined with one another in any desired fashion, provided that they are not obviously mutually exclusive.

BRIEF DESCRIPTION OF THE DRAWING

The invention, and advantageous embodiments and developments thereof, are described in more detail and explained below using the examples illustrated in the drawing. The features to be taken from the description and the drawing can be applied individually on their own or in any number in any combination according to the invention. In the drawings.

WAYS OF IMPLEMENTING THE INVENTION

Figure 1:
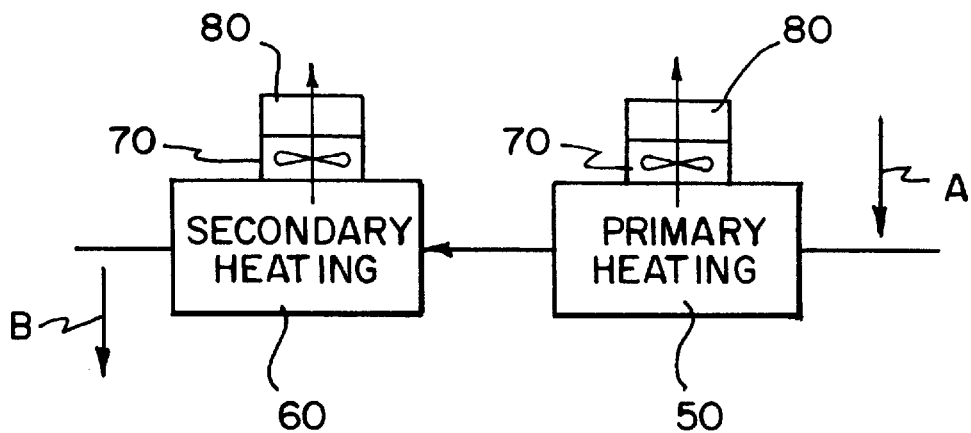
FIG. 1 shows a schematic illustration of the sequence of the process for disinfection and FIG. 2 shows a schematic construction of a device for treating screenings of one design variant of a device for treating screenings having a microwave device and a conveying device.

In the process sequence, illustrated schematically in FIG. 1, for disinfecting screenings, the latter are fed in a first process step to a first station 50 via conveying means that are not illustrated (according to arrow A), in which station the screenings are heated by means of microwave radiation. In a second process step in a second station 60, the temperature is maintained for a predeterminable period, so that the screenings can be reliably disinfected and the killing of viruses can be ensured. After this, the screenings are discharged (according to arrow B). The first station 50 and the second station 60 can also be combined into a single station, the screenings, after having been heated, then remaining in this station for a sufficient time, within which the necessary temperature for disinfection is maintained.

The transporting means can be constructed as pushing or pulling transporting means, in particular as a conveyor screw. Sliding transport of the screenings is also conceivable. The arrangement of the transporting direction of the screenings may be horizontal, as illustrated schematically in FIG. 1. A vertical or inclined transporting direction can also be implemented without problems, so that the constructional components for the disinfection can be adapted without problems to the respective constructional space conditions.

In FIG. 1, schematically above the first and second station, an air movement unit, which is designed as a low-pressure fan 70, is connected to the interior of the respective station. Adjoining the low-pressure fan 70 is a filter unit 80, which prevents an unpleasant smell from being produced outside the device. The low-pressure fan produces in the device an airstream, which is in particular heated, so that a convective drying process is initiated, which results both in the weight of the finally treated screenings being reduced, and the necessary further removal of the screenings following the treatment being able to be handled more cleanly as a result of the dryness of the material. In the case of the drying process illustrated above, the air is guided through in a one-pass process. However, air guidance in a circulation process is also conceivable, which leads to savings in energy.

Figure 2:
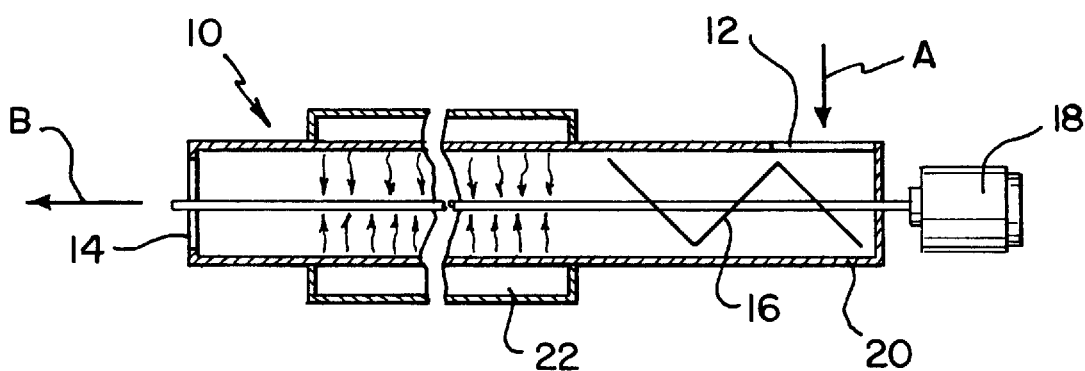

A device 10, illustrated in FIG. 2, for treating, in particular disinfection, of screenings from the mechanical cleaning stage of a sewage treatment plant has a housing 20, into which screenings are input in an inlet area 12 in accordance with arrow direction A, and the screenings are discharged once more in a discharge area 14, illustrated on the left in FIG. 1, in accordance with arrow B. Provided inside the housing 20 is a conveying device 16, which is constructed as a conveying screw and driven by a drive unit 18 arranged outside the housing 20. The housing 20 is equipped in a predetermined area with a microwave device 22, which emits its microwave radiation into the interior of the device 10 and onto the screenings. The conveyor screw transports the screenings as far as the microwave device 22. The screenings are then moved into the microwave device by pushing and subsequently moved out. In the area of the microwave device 22, the wall of the housing 20 is constructed such that said wall is transparent for the microwave radiation. The housing 20 serves as a cavity resonator in the area of the microwave device 22, the microwaves themselves being fed into this cavity area by a magnetron. The heating of the screenings and hence the disinfection or killing of viruses occurs because, as a result of dielectric losses in the screenings, energy is drawn from the microwave field and is converted into heat.

In a design variant that is not illustrated, in the area where the screenings are acted on, microwave temperature sensors are provided that measure the temperature in the screenings. On the basis of the measured values, which are emitted to a control unit, the energy density that is applied to the screenings is then set.

Reliable disinfection is carried out as a result of the fact that the microwaves are applied to the screenings for a predeterminable, adequate period.

A comprehensive process according to the invention for treating screenings is provided by the combination of the following process steps:

washing, pressing, disinfection, drying, compacting.

I claim:

1. A process for treating screenings from the mechanical cleaning stage of a sewage treatment plant, comprising the steps of:

(a) disinfecting the screenings by applying microwaves in the frequency range between 1 GHz (gigahertz) and 1 THz (terahertz) to the screenings for a predetermnined period;

(b) drying the screenings by convection during the disinfecting step by subjecting the screenings to an airstream;

(c) performing at least one of the steps of washing the screenings and pressing the screenings before the disinfecting step; and (d) compacting the screenings after the disinfecting step.

2. The process as claimed in claim 1, wherein the microwaves have a frequency range between 2.425 and 2.475 GHz (gigahertz).

3. The process as claimed in claim 1, wherein:

the disinfecting step comprises a heating-up phase, wherein the applied microwaves increase the temperature of the screenings, and a heat-maintaining phase, wherein the applied microwaves maintain the temperature of the screenings;

the process further comprising the steps of:

applying a magnetic field with a first energy density to the screenings during the heating-up phase; and applying a magnetic field with a second energy density to the screenings during the heat-maintaining phase, the second energy density being lower then the first energy density.

* * * * *